United States Patent
Choudhary et al.

(10) Patent No.: US 7,022,888 B2
(45) Date of Patent: Apr. 4, 2006

(54) PROCESS FOR THE SIMULTANEOUS CONVERSION OF METHANE AND ORGANIC OXYGENATE TO $C_2$ TO $C_{10}$ HYDROCARBONS

(75) Inventors: Vasant Ramchandra Choudhary, Maharashtra (IN); Kartick Chandra Mondal, Maharashtra (IN); Shafeek Abdul Rashid Mulla, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 432 days.

(21) Appl. No.: 10/397,849

(22) Filed: Mar. 27, 2003

(65) Prior Publication Data

US 2004/0192990 A1 Sep. 30, 2004

(51) Int. Cl.
*C07C 1/20* (2006.01)
(52) U.S. Cl. .................. 585/639; 585/640; 585/943
(58) Field of Classification Search ............... 585/639, 585/640, 943
See application file for complete search history.

(56) References Cited

U.S. PATENT DOCUMENTS 5,026,937 A 6/1991 Bricker
5,336,825 A 8/1994 Choudhary et al.

*Primary Examiner*—Thuan D Dang
(74) *Attorney, Agent, or Firm*—Nixon & Vanderhye P.C.

(57) ABSTRACT

A process for the non-oxidative conversion of methane simultaneously with the conversion of an organic oxygenate, represented by a general formula: $C_nH_{2n+1}OC_mH_{2m+1}$, wherein C, H and O are carbon, hydrogen and oxygen elements, respectively; n is an integer having a value between 1 and 4; and m is an integer having a value between zero and 4, to $C_{2+}$ hydrocarbons, particularly to gasoline range $C_6$–$C_{10}$ hydrocarbons and hydrogen, using a bifunctional pentasil zeolite catalyst, having strong acid and dehydrogenation functions, at a temperature below 700° C. is disclosed. In this process the moles of methane converted per mole of oxygenate converted is above 1.0, depending upon the process conditions.

13 Claims, No Drawings

PROCESS FOR THE SIMULTANEOUS CONVERSION OF METHANE AND ORGANIC OXYGENATE TO $C_2$ TO $C_{10}$ HYDROCARBONS

FIELD OF THE INVENTION

This invention relates to a process for the production of $C_2$–$C_{10}$ hydrocarbons and hydrogen simultaneously from methane and organic oxygenate(s). This invention particularly relates to a process for the production of $C_2$–$C_{10}$ hydrocarbons, particularly gasoline range $C_5$–$C_{10}$ hydrocarbons and hydrogen by the catalytic non-oxidative conversion of methane, simultaneously with the conversion of organic oxygenate(s), such as aliphatic alcohols and ethers, to gasoline range hydrocarbons using a bifunctional pentasil zeolite catalyst, having strong acidic and dehydrogenation functions.

The process of this invention is useful in petroleum and petrochemical industries for production of $C_2$–$C_{10}$ hydrocarbons; particularly gasoline range hydrocarbons, from natural gas, particularly that produced during the oil production in remote places, and also from methane produced in the number of petroleum refining and petrochemical processes.

BACKGROUND OF THE INVENTION

Methane is the major constituent of natural gas and also of biogas. World reserves of natural gas are constantly being upgraded and more and more natural gas is currently being discovered than oil. Because of the problems associated with transportation of a very large volume of gas, most of the natural gas produced along with oil, particularly, at remote places, and the methane produced in petroleum refining and petrochemical process are flared and hence wasted. Both methane and $CO_2$ are green house gases, responsible for global warming. Hence, in future the flaring of natural gas produced during the oil production and methane produced in the petroleum refining and petrochemical processes would not be allowed and hence the methane or natural gas is to be converted to useful value-added and easily transportable product like liquid hydrocarbons of gasoline range. The conversion of methane directly to higher hydrocarbons and aromatics is extremely difficult. If technologies are made available for the conversion of the natural gas or methane to easily transportable less volatile value added products such as aromatic hydrocarbons, a far reaching economic impact can be achieved which will also lead to exploration of more gas-rich field and also natural gas hydrates increasing the natural gas reserves.

Gasoline and aromatic hydrocarbons are an important commodity in the petroleum and petrochemical industries. The most commercially important aromatics are benzene, toluene, ethyl benzene and xylenes. Aromatics are currently produced by catalytic reforming of various petroleum feed stocks and catalytic cracking of naphtha. Aromatics can also be produced by catalytic conversion of alcohols (particularly methanol), olefins or lower alkanes (particularly propane, butanes or LPG). The catalyst used in these processes (methanol-to-gasoline Mobil's MTG process, olefins-to-gasoline-and-distillate or MOGD or M2 forming, both developed by Mobil Oil, and LPG-to-aromatics conversion process or Cyclar Process developed by UOP) belong to the pentasil zeolite family, particularly that having ZSM-5 structure.

An oxidative activation of methane for converting it directly to $C_2$-hydrocarbons, ethane and ethylene, is known in the prior art and it is described in a book {E. E. Wolf "Methane Conversion by Oxidative Process: Fundamental and Engineering Aspects" Van Nostrand Trinhold Catalysis Series, New York, (1992)} and also in a number or review articles {J. R. Aderson, Appl. Catal., 47 (1989) 177, J. S. Lee et. al., Catal. Rev. -Sci. Eng., 30 (1988) 249; G. J. Hutchings et. al., Chem. Soc. Rev., 18 (1989) 25; J. H. Lunsford, Catal. Today 6 (1990) 235; J. H. Lunsford, Angew. Chem. Intl. Ed. Engl. 34 (1995)970}.

According to a recent U.S. Pat. No. 5,336,825 (1984) of Choudhary V. R. and co-workers, methane can be converted to gasoline range hydrocarbons comprising aromatic hydrocarbons by carrying out the conversion of methane in the following two steps. Step (i): Catalytic oxidative conversion of methane to ethylene and minor amounts of $C_3$ and $C_4$ olefins in presence of free oxygen using a basic solid catalyst at a temperature preferably between 600° C. and 850° C. Step (ii): catalytic conversion of ethylene and higher olefins formed in the step (i) to liquid hydrocarbons of gasoline range over an acidic solid catalyst containing high silica pentasil zeolite, using product stream of the step (I) as the feed.

In the other multistep processes as described in Eur, Pat. Appln. EP 516,507 (1992) and Fr. Appl. 91/6,195 (1991), a methane rich fraction of natural gas is selectively oxidized, mixed with a $C_{2+}$ hydrocarbon rich natural gas fraction, pyrolized and then the mixture is aromatized with a catalyst based on zeolite and gallium.

All the prior art teach the process for the oxidative activation of methane involves the following undesirable highly exothermic methane combustion reactions:

$$CH_4 + 2O_2 \rightarrow CO_2 + 2H_2O \qquad (1)$$

$$CH_4 + 1.5O_2 \rightarrow CO + 2H_2O \qquad (2)$$

Hence, these processes are hazardous in nature. Moreover, in these processes, undesirable carbon oxides, CO and $CO_2$, are formed thus reducing the product selectivity and also creating environmental pollution problems and global warming by the release of $CO_2$ in the atmosphere.

High temperature non-oxidative conversion of methane to $C_{2+}$ hydrocarbons is known in the prior art.

It has been known for a long time that methane and natural gas can be pyrolytically converted to benzene at temperatures above 899° C. (1659° F.), preferably above 1200° C.

A paper on "High Temperature Synthesis of Aromatics Hydrocarbons from Methane" published in Science 153 (1966) 1393 disclosed that aromatic hydrocarbons can be prepared from methane by contact with silica at 1000° C. The yield of hydrocarbons was in the range of 4.8–7.2% based on the methane used in the single pass at a gas space velocity of 1224 $h^{-1}$.

More recent, a non-oxidative activation of methane by dehydrogenative coupling of methane over active carbon at temperature $\leq 1100°$ C. has been reported by H. Yagita et. al. [H. Yagita et. al., in Environmental Catalysis, G. Centi et. al. Eds. SCI Publication, Rome, 1995, page 639–642].

U.S. Pat. No. 4,814,533 (1989) discloses a continuous catalytic process for the production of higher molecular weight hydrocarbons rich in ethylene or aromatics or both from lower molecular weight hydrocarbons or methane in which a lower molecular weight hydrocarbon containing gas is contacted in a reaction zone with a higher molecular weight hydrocarbon synthesis catalyst at a temperature greater than 1000° C.

A recent Japanese Patent, Jpn. Kokai Tokkyo Koho JP. 07,155,600 (1995), discloses a process for the preparation of reaction media for aromatization and preparation of aromatics from methane at high temperature. The reaction media, which is prepared by thermal decomposition of cyclohexane at 1050° C., was fed with methane at 1050° C. for 2 h to give benzene in 54.7% selectivity at 30.9% conversion.

Because of the requirement of a high temperature for the conversion of methane and also due to the extensive coke formation at the high reaction temperature, the above processes based on the non-oxidative conversion of methane are difficult to practice and hence uneconomical.

Catalytic aromatization of methane in the absence of $O_2$ using zeolite catalyst is also known in the prior art.

U.S. Pat. No. 4,727,206, GB Patent 8531687 and European Patent Application No. 0 228 267 A1 disclosed the aromatization of methane by contacting with gallium loaded zeolite containing group VII B metal or metal compound as a catalyst at a temperature from 600° C. to 800° C., preferably from 650° C. to 775° C., in the absence of oxygen. However, the conversion of methane into aromatics and the yield of the aromatics reported in the examples of these patents, are very low. At a weight hourly space velocity of 1.0 and absolute pressure of 7.0 bar, methane conversion at 675° C., 700° C. and 750° C. was 3.6 wt. %, 4.9 wt. % and 8.3 wt. %, respectively and aromatics yield was 2.0 wt. %, 2.53 wt. % and 2.95 wt. %, respectively. Because of the very low aromatics yield even at a temperature as high as 750° C., this process cannot be economically practiced.

A U.S. Pat. No. 5,026,937 (1991) discloses a process for the aromatization of methane using a catalyst comprising about 0.1 to about 2 wt. % gallium containing ZSM zeolite and phosphorus-containing alumina, at a gas hourly space velocity of 400–1500 $h^{-1}$ at relatively low temperature conditions. As per the illustrated example of this process, when the catalyst was contacted with a stream of 100 mole % methane at a flow rate of 1.4 $h^{-1}$ LHSV (liquid hourly space velocity) at 750° C. and at atmospheric pressure, the overall methane conversion was 3.5 mole % in the single pass, the selectivity to $C_{2+}$ hydrocarbons was 72%, and the selectivity to coke was 28%. Because of the very low methane conversion even at 750° C. and low space velocity and also due to the very high selectivity to coke, this process is not economical. Because of the extensive coke formation, this process is also difficult to practice on a commercial basis.

Although aromatization of methane at a temperature below 700° C. is desirable for making the conversion of methane-to-aromatics process commercially more feasible, the aromatization of methane alone at the low temperatures is not at all thermodynamically possible. At a temperature below 700° C., the conversion of methane to benzene proceeds according to following reaction, $$6CH_4 \rightarrow C_6H_6 + 9H_2 \quad (3)$$

and involves a very large free energy change, $\Delta G_r$. The value of $\Delta G_r$, which is greater than 35 kcal per mole of benzene formed at or below 700° C., is much larger than zero. This high thermodynamic barrier does not allow the formation of benzene from methane at the lower temperatures. Hence, for the conversion of methane to aromatics at or below 700° C., it is necessary to find ways for overcoming the thermodynamic barrier and especially for the non-oxidative conversion of methane, which is the most inert of all of the hydrocarbons, at lower temperatures.

A number of U.S. Pat. Nos. 3,928,483 (1975), 3,931,349 (1976), and 4,05,576 (1977), 4,046,825 (1977), and 4,138, 440(1979), assigned to Mobil oil corporation disclosed process for the production of gasoline from methanol, other alcohol and ether, using shape selective ZSM-5 zeolite catalyst. A commercial plant based on Mobil's methanol-to-gasoline (MTG) process, involving production of methanol from methane via syngas route: methane steam reforming to syngas and syngas conversion to methanol, was also successfully operated in New Zealand in 1985. However, the process economics was then not favourable to sustain the gasoline production. Since the commercial plant could not be operated economically, it was shut-down [Ref. J. Haggin, Methane-to-Gasoline Plant Adds to New Zealand Liquid Fuel Resources, Chemical & Engineering News page 22, Jun. 22, 1987; J. H. Lunsford, The Catalytic Conversion of Methane to Higher Hydrocarbons. Catal. Today, vol. 6 page 235, (1990)]. It is therefore of the great challenge to inventors to develop not only technically feasible but also economically feasible process for the conversion of methane to higher hydrocarbons by finding a novel way for non-oxidative activating chemically inert methane, particularly at lower temperatures, below 700° C.

OBJECTS OF THE INVENTION

The main object of the present invention is therefore to provide a novel process for non-oxidative activation of methane at low temperature (below 700° C.) and to convert methane to higher hydrocarbons.

Another object of the invention is to provide a process for conversion of methane to higher hydrocarbons at temperature below 700° C., overcoming the thermodynamic barrier.

SUMMARY OF THE INVENTION

The process of the present invention has been developed on the basis of our findings that in the presence of a bifunctional zeolite catalyst having dehydrogenation and acidic properties and in the presence of an aliphatic alcohol and/or ether with methane to alcohol or ether ratio above 0.5, the conversion of methane into higher hydrocarbons takes place at a temperature below 700° C., overcoming the thermodynamic barrier. The moles of methane converted per mole of alcohol or ether converted is found to be as high as 2.6 under the particular set of conditions.

The conversion of methane in the process of the present invention can be explained by the alkylation reactions between methane and the alcohol or ether over the bifunctional zeolite (Ga-modified ZSM-5 zeolite), involving the activation of methane in the presence of alcohol or ether as follows:

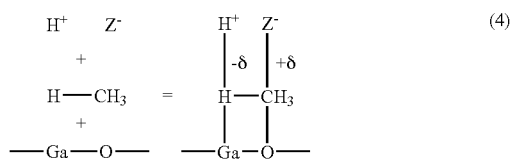
(4)

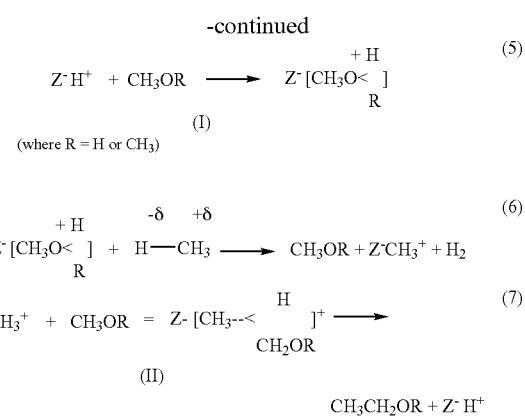

The activation of methane is expected to result from a combined effect of the Ga-oxide species and zeolite protons or acid-base pairs ($Z^-H^+$). The formation of methyl cations is then facilitated in the presence of oxonium cation (I), ultimately leading to the formation of penta coordinated carbocations (II).

Because of the involvement of high free energy change, $\Delta G_r > 35$ kcal/mole of benzene, according to reaction 3, the direct formation of benzene from methane below 700° C. is not possible thermodynamically. The thermodynamic barrier is, however, drastically reduced or even eliminated because of the addition of an aliphatic alcohol or ether in the feed; the value of $\Delta G_r$ approaches to zero or even becomes negative, depending upon the additive and its concentration relative to that of methane and the temperature.

SUMMARY OF THE INVENTION

It has now been found by the present inventors due to exclusive research work that, by adding at least one aliphatic alcohol or ether or both to methane in the presence of a bifunctional pentasil zeolite catalyst, having strong dehydrogenation and acid sites, the thermodynamic barrier for the aromatization of methane is overcome and the non-oxidative activation of methane, leading to its conversion to higher hydrocarbons, occurs below 700° C. temperature.

The present invention provides a process for the simultaneous conversion of methane and organic oxygenate(s), represented by a general formula: $C_nH_{2n+1}OC_mH_{2m+1}$ wherein, C, H and O are carbon, hydrogen and oxygen elements, respectively; n is an integer having a value between 1 and 4; and m is an integer having a value between zero and 4, to $C_2$–$C_{10}$ hydrocarbons and hydrogen, the process comprises:

i) contacting with a bifunctional pentasil zeolite catalyst essentially comprising at least one metallic element, selected from a group consisting of Ga, In, Zn, Fe, Mo, Ag, Au, noble metals and rare earth elements, having strong acidic and dehydrogenation sites, a gaseous feed comprising methane and at least one organic oxygenate, with or without an inert gas, with a methane to organic oxygenate mole ratio above 0.5, at a gas hourly space velocity in the range from 100 $cm^3g^{-1}h^{-1}$ to 10,000 $cm^3g^{-1}h^{-1}$, at a temperature below 700° C. and at a pressure of at least 1 atm, such that the ratio of moles of methane converted to moles of organic oxygenate in the feed is at least 0.05;

ii) condensing the normally liquid products from the products stream obtained from step-i and separating liquid hydrocarbons and water from condensed liquid products;

iii) separating hydrogen from the gaseous products obtained from step-ii; and iv) recycling to step-i the gas stream obtained from step-iii, with or without the separation of normally gaseous $C_{2+}$ hydrocarbons.

In the another embodiment of the invention, the zeolite catalyst is selected from Ga-and/or In-modified ZSM-5 type zeolites, such as Ga and/or In-impregnated H-ZSM-5, Ga- and/or In-exchanged ZSM-5, H-galloaluminosilicate of ZSM-5 type structure and H-gallosilicate of ZSM-5 type structure.

In the another embodiment of the invention, the organic oxygenate is selected from a group of organic oxygenates, such as methanol, ethanol, dimethyl ether and diethyl ether.

In the another embodiment of the invention, the organic oxygenate is methanol or ethanol.

In the another embodiment of the invention, the methane to organic oxygenate mole ratio in the gaseous feed is between 1 and 25.

In the another embodiment of the invention, the gas hourly space velocity of the gaseous feed is between 500 $cm^3g^{-1}h^{-1}$ and 5000 $cm^3g^{-1}h^{-1}$.

In the other embodiment of the invention, the temperature employed in step-i is between 350° C. and 650° C.

In the another embodiment of the invention, the ratio of inert gas to methane in the feed in step-i is between zero to 1.

In the another embodiment of the invention, the reaction in step-i is carried out in a single or multiple fixed-bed reactor or fluid bed reactor or moving bed reactor.

The main finding of this invention is that methane can be activated non-oxidatively and converted to higher hydrocarbons along with the conversion of an organic oxygenate, such as aliphatic alcohol or ethers, to aromatics at a low temperature (below 700° C.), using bifunctional pentasil zeolite catalyst having strong acidic and dehydrogenation functions. Other finding of this invention is that the moles of methane conversion per mole of oxygenate converted could be above 1.0, as high as 2.6 depending upon the process conditions.

DETAILED DESCRIPTION OF THE INVENTION

The present invention provides a process for the simultaneous conversion of methane and organic oxygenate(s), represented by a general formula: $C_nH_{2n+1}OC_mH_{2m+1}$ wherein, C, H and O are carbon, hydrogen and oxygen elements, respectively; n is an integer having a value between 1 and 4; and m is an integer having a value between zero and 4, to $C_2$–$C_{10}$ hydrocarbons and hydrogen, the process comprise:

i) contacting with a bifunctional pentasil zeolite catalyst essentially comprising at least one metallic element, selected from a group consisting of Ga, In, Zn, Fe, Mo, Ag, Au, noble metals and rare earth elements, having strong acidic and dehydrogenation sites, a gaseous feed comprising methane and at least one organic oxygenate, with or without an inert gas, with a organic oxygenate to methane to organic oxygenate mole ratio above 0.5, at a gas hourly space velocity in the range from 100 $cm^3g^{-1}h^{-1}$ to 10,000 $cm^3g^{-1}h^{-1}$, at a temperature below 700° C. and at a pressure of at least 1 atm, such that the ratio of moles of methane converted to moles of organic oxygenate in the feed is at least 0.05;

ii) condensing the normally liquid products from the products stream obtained from step-i and separating liquid hydrocarbons and water from condensed liquid products;

iii) separating hydrogen from the gaseous products obtained from step-ii; and iv) recycling to step-i the gas stream obtained from step-iii, with or without the separation of normally gaseous $C_{2+}$ hydrocarbon.

The bifunctional pentasil zeolite which may be employed in the process of the present invention may have ZSM-5, ZSM-8 or ZSM-11 type crystal structure consisting of a large number of 5-membered oxygen-rings, i.e, pentasil rings, which are more stable as compared to other O-rings. The zeolite with ZSM-5 type structure is the more preferred catalyst.

The ZSM-5, ZSM-8 and ZSM-11 type zeolite structures are all well known in the prior art and have unique shape-selective behavior. Zeolite ZSM-5 is described in greater detail in U.S. Pat. No. 3,702,886. ZSM-11 zeolite is described in U.S. Pat No. 3,709,979. ZSM-8 zeolite is described in Netherlands Patent 7,014,807 and U.S. Pat. No. 3,700,585. ZSM-5/ZSM-11 intermediate zeolite structures are described in U.S. Pat. No. 4,229,424. The term "Zeolite" used herein is not only for microporous crystalline aluminosilicate but also for microporous crystalline galloaluminosilicates and gallosilicates.

The bifunctional pentasil zeolite catalyst used may be preferably selected from the group consisting of Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. These zeolites can also be prepared by methods known in the prior art.

The bifunctional ZSM-5 type pentasil zeolite used in the process of present invention contains tetrahedral aluminium and/or gallium, which are present in the zeolite framework or lattice, and octahedral gallium or indium, which is not present in the zeolite framework but present in the zeolite channels in a close vicinity of the zeolitic protonic acid sites, which are attributed to the presence of tetrahedral aluminium and gallium in the zeolite. The tetrahedral or framework Al and/or, Ga is responsible for the acid function of zeolite and octahedral or non-framework Ga and/or In is responsible for the dehydrogenation function of the zeolite.

The most effective and efficient bifunctional pentasil zeolite which can be used in the process of the present invention is H-galloaluminosilicate of ZSM-5 type structure having framework (tetrahedral) Si/Al and Si/Ga mole ratio of about 10–100 and 15–150, respectively, and non-framework (octahedral) Ga of about 0.5–5.0 wt. %. These pentasil H-galloaluminosilicate zeolite can be prepared by procedures known in the prior art.

When pentasil H-galloaluminosilicate zeolites are used, the density of strong acid sites can be controlled by the framework Al/Si mole ratio, the higher the Al/Si ratio, the higher is the density of strong acid sites. The highly dispersed non-framework gallium oxide species can be obtained by the degalliation of the zeolite by its pretreatment with $H.sub.2$ and steam. The zeolite containing strong acid sites with high density and also highly dispersed non-framework gallium oxide species in close proximity of the zeolite acid site is preferred for the process of the present invention. The catalyst may or may not contain any binder such as alumina, silica or clay material. The catalyst can be used in the form of pellets, extrudates and particles of different shapes and sizes.

The examples of the organic oxygenate are methanol, ethanol, propanols, butanols, dimethyl ether, diethyl ether, dipropyl ether, dibutyl ether, methyl ethyl ether, methyl propyl ethers, methyl butyl ether and the like. The preferred organic oxygenate in the feed may be selected from methanol, ethanol, dimethyl ether and diethyl ether and more preferably from methanol and ethanol.

In the process of this invention, the preferred mole ratio of methane to organic oxygenate in the feed ranges from about 1.0 to about 25; the preferred gas hourly space velocity of the feed ranges from about 500 $cm^3g^{-1}h^{-1}$ to about 5,000 $cm^{-3}g^{-1}h^{-1}$; the preferred temperature ranges from 350° C. to 650° C.; and the preferred ratio of inert gas to methane in the feed is between zero to 1.0. Products of the process of this invention are mainly water, and $C_6$ and $C_{10}$ aromatics with smaller amounts of ethylene, ethane, propylene, propane and $C_4$ hydrocarbons and traces of $C_{5+}$ aliphatic hydrocarbons. Water is formed by dehydration of said organic oxygenate. The presence of oxygenate in the feed is essential in the process of this inventions. In absence of said organic oxygenate methane is not converted in the process of this invention. The role of the bifunctional pentasil zeolite catalyst is to activate both methane and said oxygenate and convert then into the products. The carbon deposited on the catalyst of the process of this invention can be removed by oxidizing it by an oxygen containing gas. In the process of this invention, the feed comprising methane and said one or more organic oxygenates may be contacted with the catalyst in a single or multiple fixed bed reactors, fluid bed reactor or moving bed reactor, known in the prior art.

In the process of this invention, the normally gaseous products from the normally liquid products are separated from each other by known prior art method. Also, the water from the liquid products and the hydrogen from the gaseous products are separated by method known in the prior art. Terns used in this specification have following meanings.

Framework Si means Si present in the lattice of the zeolite.

Framework Al or Ga means the Tetrahedral Al or Ga present in the lattice of the zeolite.

Non-framework Ga means octahedral Ga present in the zeolite channels.

Gas hourly space velocity, (GHSV) means volume of feed gases, measured at 0° C. and 1 atm pressure, passed over a unit mass of catalyst per hour.

Conversion, %, means weight percent of a particular reactant converted to all the products.

Product Selectivity, %=[(percent of reactant or reactants converted to a particular product÷percent of reactant or reactants converted to all products)]×100.

When nitrogen is used in the feed of the invented process, the methane conversion (%) was obtained from the $CH_4/N_2$ mole ratios in the feed and products as follows:

Methane conversion (%)=100×[$(CH_4/N_2)_{feed}$−$(CH_4/N_2)_{product}$]÷[$(CH_4/N_2)_{feed}$]

Conversion given in the examples is per pass conversion.

The present invention is described with reference to the examples given below which are provided to illustrate the invention only and, therefore, should not be construed to limit the scope of the invention.

EXAMPLE 1

This example illustrates the catalytic process of the present invention for the low temperature non-oxidative conversion of methane and thereby converting it directly to higher hydrocarbons or aromatics using methanol as an additive in the feed comprising methane, and using ZSM-5 type H-galloaluminosilicate zeolite having bulk Si/Ga=24.3, bulk Si/Al=40.3, framework Si/Ga=49.9, framework Si/Al=40.3, Na/(Al+Ga)=0.03, non-framework Ga=0.32 mmol g$^{-1}$, crystal morphology or shape=spherical-hexagonal, crystal size=5.5±1.5 μm and strong acid sites measured in terms of pyridine chemisorbed at 400° C.=0.46 mmol g$^{-1}$. All the ratio are mole ratios. The zeolite was prepared by process described in European Patent Application EP 0124271 and in the reference: Choudhary et. al. J. Catal. 158 (1996) 23.

A conventional tubular quartz reactor of 12 mm internal diameter packed with the zeolite catalyst of 30–52 mesh size particles and kept in the tubular electrical furnace such that the catalyst is in a constant temperature zone of the furnace, was used for illustrating the process. The catalytic process is carried out by passing continuously a mixture of methane and N$_2$ with or without methanol additive in the feed over the zeolite catalyst at the process conditions given in Table 1. The reactor or reaction temperature was measured by Chromel-Alumel thermocouple located axially in the catalyst bed. The reaction gaseous products after the removal of water and normally liquid hydrocarbons formed in the reaction by condensation at 2° C., the liquid hydrocarbons and the feed were analyzed by an on-line gas chromatograph with thermal conductivity and flame ionized detectors and computing integrator, using a 3 mm×3 m Poropak-Q column for separating C$_1$–C$_4$ hydrocarbons and using a 3 mm×5 m column containing 5% Benton-34–5% dinonyphthalate on chromosorb-W for separating aromatic hydrocarbons. Conversion data were obtained from the feed and product composition, as follows conversion (%)={(moles of reactant in the feed–moles of reactant in the products)÷(moles of reactant in the feed hydrocarbons)}×100.

The results are presented in Table 1. The results in the Table 1 clearly show that, in the absence of methanol (experiment no. 2), the conversion of methane in the process is zero and hence there is no conversion of methane at 600° C. and consequently below 600° C. But when methanol is added to the feed (experiment no. 1), the thermodynamic barrier is overcome and the methane from the feed is activated even at 540° C. and thereby it is converted to higher hydrocarbons or aromatics with a high ratio of methane converted per mole of methanol converted. The methanol additive from the feed is completely converted to hydrocarbons, water and hydrogen. There was no formation of carbon dioxide in the reaction.

TABLE 1

Results of the conversion of methane to C$_{2+}$ hydrocarbons and hydrogen in the presence and absence of methanol in the feed.

| | Experiment no.: | |
|---|---|---|
| | 1 | 2 |
| Reaction conditions | | |
| Methanol/Methane mole ratio in feed | 0.15 | 0.0 |
| N$_2$/Methane mole ratio in feed | 0.08 | 0.08 |
| Feed gas space velocity (cm$^3$g$^{-1}$h$^{-1}$) | 1090 | 1090 |
| Temperature (° C.) | 540 | 600 |
| Pressure (atm) | 1.3 | 1.3 |
| Conversion of methane (%) | 10.1 | 0.0 |
| Conversion of methanol (%) | 100 | — |
| Methane converted/methanol converted (mol/mol) ratio | 0.70 | — |
| Distribution of hydrocarbons in the hydrocarbon products (wt. %) | | |
| Methane | 81.4 | 100 |
| Ethylene | 0.46 | 0.0 |
| Ethane | 0.17 | 0.0 |
| C$_3$ hydrocarbons | 0.52 | 0.0 |
| C$_4$ hydrocarbons | 0.05 | 0.0 |
| C$_{5+}$ aliphatics | 0.02 | 0.0 |
| Benzene | 1.29 | 0.0 |
| Toluene | 5.99 | 0.0 |
| C$_8$ aromatics | 7.16 | 0.0 |
| C$_9$ aromatics | 2.84 | 0.0 |
| C$_{10}$ aromatics | 0.14 | 0.0 |
| H$_2$ produced (mmol · g$^{-1}$h$^{-1}$) | 7.5 | 0.0 |

EXAMPLES—2 to 9

These examples illustrate the influence of process conditions, such as methane/methanol mole ratio in the feed, reaction temperature and gas hourly space velocity, GHSV, on the conversion of methane and methanol present in the feed and also on the methane converted per mole of methanol converted in the process of this invention. The catalytic process of this invention was carried out by the reactor and procedures described in EXAMPLE-1 and using the catalyst of Example-1, at the different process conditions, given in Tables 2 and 3. The results are presented in Tables 2 and 3.

TABLE 2

Results of the simultaneous conversion of methane and methanol over the catalyst of Example 1 at different process conditions

| | Example No. | | | |
|---|---|---|---|---|
| | 2 | 3 | 4 | 5 |
| | Catalyst used | | | |
| | Catalyst of Example 1 | Catalyst of Example 1 | Catalyst of Example 1 | Catalyst of Example 1 |
| | Organic oxygenate used | | | |
| Reaction conditions | Methanol | Methanol | Methanol | Methanol |
| Methane/methanol mole ratio in feed | 23.8 | 24.0 | 11.9 | 6.8 |
| N$_2$/methane mole ratio in feed | 0.083 | 0.084 | 0.082 | 0.080 |
| GHSV (cm$^3$g$^{-1}$h$^{-1}$) | 1080 | 1080 | 1080 | 1070 |
| Temperature (° C.) | 560 | 532 | 558 | 540 |
| Pressure (atm) | 1.3 | 1.3 | 1.2 | 1.3 |
| Conversion of methane (%) | 10.8 | 10.6 | 9.2 | 10.9 |
| Conversion of methanol (%) | 100 | 100 | 100 | 100 |
| Methane converted/methanol converted (mol/mol) ratio | 2.6 | 2.5 | 1.1 | 0.74 |

TABLE 3

Results of the simultaneous conversion of methane and methanol over the catalyst of Example 1 at different process conditions

| | Example No. | | | |
|---|---|---|---|---|
| | 6 | 7 | 8 | 9 |
| | Catalyst used | | | |
| | Catalyst of Example 1 | Catalyst of Example 1 | Catalyst of Example 1 | Catalyst of Example 1 |
| | Organic oxygenate used | | | |
| Reaction conditions | Methanol | Methanol | Methanol | Methanol |
| Methane/methanol mole ratio in feed | 6.9 | 7.0 | 6.8 | 6.9 |
| $N_2$/methane mole ratio in feed | 0.081 | 0.084 | 0.05 | 0.0 |
| GHSV ($cm^3 g^{-1} h^{-1}$) | 2700 | 540 | 550 | 1795 |
| Temperature (° C.) | 545 | 470 | 530 | 585 |
| Pressure (atm) | 1.4 | 1.2 | 1.3 | 1.2 |
| Conversion of methane (%) | 9.8 | 4.7 | 10.6 | 11.8 |
| Conversion of methanol to hydrocarbons (%) | 100 | 100 | 100 | 100 |
| Methane converted/methanol converted (mol/mol) ratio | 0.71 | 0.3 | 0.72 | 0.82 |

EXAMPLES—10 to 13

These examples illustrates the use of the ethanol instead of methanol as an organic oxygenate additive to the feed comprising methane in the process of this invention.

The catalytic process of this invention was carried out by the procedure described in the EXAMPLE-1 and using the same catalyst and reactor described in EXAMPLE-1, except at ethanol is used instead of methanol and process conditions are different, as given in Table 4. The results are presented in Table 4.

TABLE 4

Results of the simultaneous conversion of methane and ethanol over the catalyst of Example 1 at different process conditions

| | Example No. | | | |
|---|---|---|---|---|
| | 10 | 11 | 12 | 13 |
| | Catalyst used | | | |
| | Catalyst of Example 1 | Catalyst of Example 1 | Catalyst of Example 1 | Catalyst of Example 1 |
| | Organic oxygenate used | | | |
| Reaction conditions | Ethanol | Ethanol | Ethanol | Ethanol |
| Methane/ethanol mole ratio in feed | 9.8 | 9.7 | 9.8 | 9.6 |
| $N_2$/methane mole ratio in feed | 0.082 | 0.084 | 0.083 | 0.081 |
| GHSV ($cm^3 g^{-1} h^{-1}$) | 1040 | 1040 | 1040 | 1080 |
| Temperature (° C.) | 615 | 480 | 580 | 560 |
| Pressure (atm.) | 1.3 | 1.3 | 1.3 | 1.2 |
| Conversion of methane (%) | 15.3 | 2.2 | 13.2 | 5.1 |
| Conversion of ethanol to hydrocarbons (%) | 100 | 100 | 100 | 100 |
| Methane converted/thanol converted (mol/mol) ratio | 1.5 | 0.21 | 1.3 | 0.5 |

EXAMPLES—14 to 17

These examples illustrates the use of the diethyl ether instead of methanol as an organic oxygenate additive to the feed comprising methane in the process of this invention.

The catalytic process of this invention was carried out by the procedure described in the EXAMPLE-1 and using the same catalyst and reactor described in EXAMPLE-1, except then diethyl ether is used instead of methanol and process conditions are different, as given in Table 5. The results are presented in Table 5.

TABLE 5

Results of the simultaneous conversion of methane and diethyl ether over the catalyst of Example 1 at different process conditions

| | Example No. | | | |
|---|---|---|---|---|
| | 14 | 15 | 16 | 17 |
| | Catalyst used | | | |
| | Catalyst of Example 1 | Catalyst of Example 1 | Catalyst of Example 1 | Catalyst of Example 1 |
| | Organic oxygenate used | | | |
| Reaction conditions | Diethyl ether | Diethyl ether | Diethyl ether | Diethyl ether |
| Methane/diethyl ether mole ratio in feed | 17.5 | 17.4 | 17.5 | 17.3 |
| $N_2$/methane mole ratio in feed | 0.08 | 0.08 | 0.08 | 0.08 |
| GHSV ($cm^3 g^{-1} h^{-1}$) | 1090 | 1090 | 1095 | 1100 |
| Temperature (° C.) | 633 | 560 | 610 | 650 |
| Pressure (atm.) | 1.3 | 1.2 | 1.3 | 1.2 |
| Conversion of methane (%) | 14.3 | 3.7 | 12.8 | 8.5 |
| Conversion of diethyl ether to hydrocarbons (%) | 100 | 100 | 100 | 100 |
| Methane converted/iethyl ether converted (mol/mol) ratio | 1.61 | 0.42 | 1.44 | 1.0 |

EXAMPLES—18 to 21

These examples further illustrate the process of this invention, using, Ga/H-ZSM-5 zeolite catalyst (with Si/Al=35, Ga-loading: 1.0 wt. %, strong acid sites measured in terms of pyridine chemisorbed at 400° C.=0.28 mmol. $g^{-1}$). The preparation and characterization of the zeolite catalyst are given elsewhere [ref. Choudhary, et.al. Microporous Mesoporous Material 37 (2000) 1–8]

The process over the catalyst was carried out using the reactor and procedures similar to that used in Example 1 at the process conditions given in Table 6. The results are presented in Table 6.

TABLE 6

Results of the simultaneous conversion of methane and methanol over the Ga/H-ZSM-5 catalyst at different process conditions

| | Example No. | | | |
|---|---|---|---|---|
| | 18 | 19 | 20 | 21 |
| | Organic oxygenate used | | | |
| Reaction conditions | Methanol | Methanol | Methanol | Methanol |
| Methane/methanol mole ratio in feed | 6.9 | 6.8 | 6.8 | 6.8 |

TABLE 6-continued

Results of the simultaneous conversion of methane and methanol over the Ga/H-ZSM-5 catalyst at different process conditions

| | Example No. | | | |
|---|---|---|---|---|
| | 18 | 19 | 20 | 21 |
| | Organic oxygenate used | | | |
| Reaction conditions | Methanol | Methanol | Methanol | Methanol |
| $N_2$/methane mole ratio in feed | 0.08 | 0.08 | 0.08 | 0.08 |
| GHSV ($cm^3g^{-1}h^{-1}$) | 1080 | 1090 | 1100 | 1040 |
| Temperature (° C.) | 560 | 610 | 580 | 530 |
| Pressure (atm.) | 1.2 | 1.3 | 1.3 | 1.4 |
| Conversion of methane (%) | 10.3 | 8.7 | 9.5 | 8.0 |
| Conversion of methanol to hydrocarbons (%) | 100 | 100 | 100 | 100 |
| Methane converted/methanol converted (mol/mol) ratio | 0.7 | 0.6 | 0.65 | 0.56 |

EXAMPLES—22 and 23

These examples further illustrate the process of this invention using In/H-ZSM-5 (with Si/Al=20, In-loading 0.11 mmolg$^{-1}$ and strong acid sites measured in terms of pyridine chemisorbed at 400° C.=0.32 mmol.g$^{-1}$) zeolite catalyst. The catalyst was prepared and characterized by the methods similar to that used for the Ga/H-ZSM-5 zeolite catalyst used in Examples—18 to 21, except that instead of gallium nitrate, Indium nitrate was used in the catalyst preparation.

The process over the catalyst was carried out using the reactor and procedures similar to that used in EXAMPLE 1 at the process conditions given in Table 7. The results are presented in Table 7.

TABLE 7

Results of the simultaneous conversion of methane and methanol over the In/H-ZSM-5 catalyst at different process conditions

| | Example No. | |
|---|---|---|
| | 22 | 23 |
| | Organic oxygenate used | |
| Reaction conditions | Methanol | Methanol |
| Methane/methanol mole ratio in feed | 6.8 | 11.9 |
| $N_2$/methane mole ratio in feed | 0.085 | 0.084 |
| GHSV ($cm^3g^{-1}h^{-1}$) | 1090 | 1080 |
| Temperature (° C.) | 503 | 530 |
| Pressure (atm.) | 1.3 | 1.4 |
| Conversion of methane (%) | 6.7 | 9.0 |
| Conversion of methanol to hydrocarbons (%) | 100 | 100 |
| Methane converted/methanol converted (mol/mol) ratio | 0.46 | 1.1 |

EXAMPLES—24 to 27

These examples illustrate the use of H-gallosilicate (ZSM-5 type) (bulk Si/Ga=30.1, concentration of non-framework Ga=1.5 wt. % and strong acid sites measured in terms of the pyridine chemisorbed at 400° C.=0.25), preparation of which described by Choudhary et. al [ref. Choudhary et.al. Appl.Catal.A: Gen 162 (1997) 239–248], in the process of this invention.

The process over the catalyst was carried out using the reactor and procedures similar to that used in EXAMPLE 1 at the process conditions given in Table 8. The results are presented in Table 8.

TABLE 8

Results of the simultaneous conversion of methane and methanol or dimethyl ether over the H-gallosilicate (ZSM-5 type) zeolite catalyst at different process conditions

| | Example No. | | |
|---|---|---|---|
| | 24 | 25 | 26 |
| | Organic oxygenate used | | |
| Reaction conditions | Methanol | Methanol | Methanol |
| Methane/methanol mole ratio in feed | 6.82 | 6.81 | 6.8 |
| $N_2$/methane mole ratio in feed | 0.084 | 0.082 | 0.083 |
| GHSV ($cm^3g^{-1}h^{-1}$) | 1075 | 1090 | 1080 |
| Temperature (° C.) | 607 | 635 | 555 |
| Pressure (atm.) | 1.3 | 1.3 | 1.3 |
| Conversion of methane (%) | 9.5 | 7.5 | 5.2 |
| Conversion of methanol to hydrocarbons (%) | 100 | 100 | 100 |
| Methane converted/methanol converted (mol/mol) ratio | 0.65 | 0.51 | 0.35 |

EXAMPLES 28 to 30

These examples further illustrate the process of this invention, using Pt. Zn.Ga/H-ZSM-5 zeolite catalyst (with Si/Al=20, loading of Pt, Zn and Ga=0.1, 1.5 and 0.7 wt. %, respectively, and strong acid sites measured in terms of the pyridine chemisorbed at 400° C.=0.33 mmol.g$^{-1}$).

The process over the catalyst was carried out using the reactor and procedures similar to that described in EXAMPLE 1 at the process conditions given in Table 9. The results are presented in Table 9.

The catalyst was prepared by impregnating 0.05 mmol of $H_2PtCl_6$, 2.3 mmoles of Zinc nitrate and 1.0 mmoles of gallium nitrate from their aqueous solution on 10 g H-ZSM-5 zeolites (with Si/Al=20 and Na/Al<0.01), drying and then calcining the impregnated zeolite at 600° C. for 2 h.

TABLE 9

Results of the simultaneous conversion of methane and methanol or ethanol or dimethyl ether over the Pt.Zn.Ga/H-ZSM-5 catalyst at different process conditions

| | Example No. | | |
|---|---|---|---|
| | 28 | 29 | 30 |
| | Organic oxygenate used | | |
| Reaction conditions | Methanol | Ethanol | Diethyl ether |
| Methane/oxygenate mole ratio in feed | 24.0 | 9.9 | 10.2 |
| $N_2$/methane mole ratio in feed | 0.082 | 0.0 | 0.083 |
| GHSV ($cm^3g^{-1}h^{-1}$) | 1100 | 1010 | 1070 |
| Temperature (° C.) | 570 | 581 | 575 |
| Pressure (atm.) | 1.3 | 1.3 | 1.3 |
| Conversion of methane (%) | 11.0 | 13.3 | 13.5 |
| Conversion of oxygenate to hydrocarbons (%) | 100 | 100 | 100 |
| Methane converted/oxygenate converted (mol/mol) ratio | 2.6 | 1.4 | 1.5 |

All the above examples illustrated that methane can be converted simultaneously with the conversion of methanol, ethanol, n-butanol, diethyl ether or dimethyl ether over bifunctional pentasil (ZSM-5) zeolite catalyst at a temperature much lower than 700° C., with the ratio of the methane converted to the oxygenate converted in the range from 0.2 to 2.5, depending upon the catalyst and process conditions employed in the process of this invention.

Novel Features and Advantages of the Process of this Invention Over the Prior Art Processes for Methane Conversion or Methanol-to-gasoline Conversion are as Follows:

i) Because of the high thermodynamic barrier, the direct conversion of methane to aromatics or higher hydrocarbons at or below 700° C. temperature in the absence of oxygen or other oxidizing agent is not possible thermodynamically. By the process of the present invention, the thermodynamic barrier is overcome and methane can be converted non-oxidatively below 700° C. temperature to higher hydrocarbons simultaneously with the aromatization of organic oxygenate, such as methanol, dimethyl ether, ethanol, diethyl ether and the like.

ii) In the process of the present invention, the catalyst used for the low temperature non-oxidation conversion is a bifunctional pentasil zeolite having both strong acid and dehydrogenation properties, which facilitate the conversion of methane to higher hydrocarbon at low temperatures and at non-oxidative conditions.

iii) By the process of this invention, the methane present in the feed can be converted to higher hydrocarbons or aromatics with a high mole ratio of the methane converted to the methanol converted. Methane converted per mole of methanol consumed in process is as high as 2.5 or more. Hence, the present process drastically enhances the economics of the prior art Methanol-To-Gasoline (MTG) conversion process.

iv) By the process of this invention, methane which is the most inert hydrocarbon and which is difficult to activate for direct conversion to higher hydrocarbons can be converted to higher hydrocarbon or aromatics at low temperatures, below 700° C.

v) Unlike the prior art processes, involving oxidative activation of methane, the process of this invention does not produce undesirable carbon dioxide, which is a green house gas, responsible for global warming. Hence, the present process is environmentally friendly.

The organic oxygenates, particularly methanol, dimethyl ether, ethanol or butanol added in the feed of this invention can be produced from natural gas and/or renewable resources; for example, methanol and dimethyl ether can be produced from natural gas or methane or biogas (obtained from renewable sources) and ethanol or butanol can be produced by fermentation using renewable natural resources.

We claim:

1. A process for the simultaneous conversion of methane and organic oxygenate(s), represented by a general formula: $C_nH_{2n+1}OC_mH_{2m+1}$ wherein, C, H and O are carbon, hydrogen and oxygen elements, respectively; n is an integer having a value between 1 and 4; and m is an integer having a value between zero and 4, to C2-$C_{10}$ hydrocarbons and hydrogen, the process comprises:

simultaneously converting oxygenates and methane to hydrogen and $C_{2-10}$ hydrocarbons by:

contacting a gaseous feed comprising methane and at least one organic oxygenate with a methane to organic oxygenate mole ratio above 0.5, with a bifunctional pentasil zeolite catalyst essentially comprising at least one metallic element selected from the group consisting of Ga, In, Zn, Fe, Mo, Ag, Au, noble metals and rare earth elements, having strong acidic and dehydrogenation sites, such that the ratio of moles of methane converted to moles of organic oxygenate in the feed is at least 0.05, to obtain a product stream;

ii. subjecting the product stream obtained in step (i) to condensation to condense normally liquid products containing liquid hydrocarbons and water therefrom, and separating the liquid hydrocarbons and water from condensed liquid products, to obtain liquid hydrocarbons and water and a gaseous product stream;

iii. separating hydrogen from the gaseous product stream obtained in step (ii); and iv. recycling the gaseous product stream after separation of hydrogen in step (iii) to step (i), with or without the separation of normally gaseous $C_{2+}$ hydrocarbons.

2. A process as claimed in claim 1 wherein the contacting in step (i) is carried out at a gas hourly space velocity in the range from 100 $cm^3g^{-1}h^{-1}$ to 10,000 $cm^3g^{-1}h^{-1}$, at a temperature below 700° C. and at a pressure of at least 1 atm.

3. A process as claimed in claim 1 wherein the zeolite catalyst comprises a ZSM-5 catalyst modified by Ga and/or In.

4. A process as claimed in claim 3 wherein the Ga and/or In modified ZSM-5 catalyst is selected from the group consisting of Ga and/or In-impregnated H-ZSM-5, Ga-and/or In-exchanged ZSM-5, H-galloaluminosilicate of ZSM-5 type structure and H-gallosilicate of ZSM-5 type structure.

5. A process as claimed in claim 1 wherein the organic oxygenate is selected from the group consisting of methanol, ethanol, dimethyl ether and diethyl ether.

6. A process as claimed in claim 5 wherein the organic oxygenate is selected from methanol and ethanol.

7. A process as claimed in claim 1 wherein the methane to organic oxygenate mole ratio in the gaseous feed is between 1 and 25.

8. A process as claimed in claim 2 wherein the gas hourly space velocity of the gaseous feed is between 500 $cm^3g^{-1}h^{-1}$ and 5000 $cm^3g^{-1}h^{-1}$.

9. A process as claimed in claim 2 wherein the temperature employed in step (i) is between 350° C. and 650° C.

10. A process as claimed in claim 1 the contacting in step (i) is carried out in the presence of an inert gas.

11. A process as claimed in claim 10 wherein the ratio of inert gas to methane in the feed in step (i) is up to 1.

12. A process as claimed in claim 1 wherein the contacting in step (i) is carried out in a single or multiple fixed-bed reactor or fluid bed reactor or moving bed reactor.

13. A process as claimed in claim 1 wherein the moles of methane conversion per mole of oxygenate converted is between 1.0 to 2.6.

* * * * *